(12) United States Patent
Huonker (10) Patent No.: US 11,730,837 B2
(45) Date of Patent: Aug. 22, 2023

(54) DEVICE FOR DELIVERING A FLUID, IN PARTICULAR A CLEANING, CARE OR DISINFECTING FLUID FOR HANDS AND A SYSTEM FOR MONITORING SUCH A DEVICE

(71) Applicant: Huonker GmbH, Villingen-Schwenningen (DE)

(72) Inventor: Hans-Georg Huonker, Villingen-Schwenningen (DE)

(73) Assignee: HUONKER GMBH, Villingen-Schwenningen (DE)

( * ) Notice: Subject to any disclaimer, the term of this patent is extended or adjusted under 35 U.S.C. 154(b) by 0 days.

(21) Appl. No.: 17/459,191

(22) Filed: Aug. 27, 2021

(65) Prior Publication Data
US 2022/0062455 A1     Mar. 3, 2022

(30) Foreign Application Priority Data

Aug. 27, 2020 (DE) .......................... 102020122427.3

(51) Int. Cl.
*A61L 2/00* (2006.01)
*A47K 5/12* (2006.01)
*A61L 2/26* (2006.01)

(52) U.S. Cl.
CPC .......... *A61L 2/0088* (2013.01); *A47K 5/1202* (2013.01); *A47K 5/1217* (2013.01);
(Continued)

(58) Field of Classification Search
CPC ...... A61L 2/0088; A61L 2/26; A61L 2202/14; A61L 2202/15; A47K 5/1202;
(Continued)

(56) References Cited

U.S. PATENT DOCUMENTS 5,695,091 A   12/1997   Winings et al.
9,700,181 B1   7/2017   Santoro et al.
(Continued)

FOREIGN PATENT DOCUMENTS

| AT | 511784 A1 | 2/2013 |
| DE | 10258272 A1 | 7/2004 |
| JP | 2019017672 A | 2/2019 |

OTHER PUBLICATIONS

Office Action dated Jan. 11, 2022, in corresponding European application No. 2119156.6.
(Continued)

*Primary Examiner* — Vishal Pancholi
(74) *Attorney, Agent, or Firm* — Nath, Goldberg & Meyer; Jerald L. Meyer (57) ABSTRACT

The present invention relates to a device (10) for delivering a fluid, in particular a cleaning, care or disinfecting fluid for hands, comprising a housing (12) which encloses a cavity (14) into which a container (18) for holding the fluid can be installed, and forms an outer housing surface (28), a pump and metering unit (20), which can be connected or is connected to the housing (12), which can be connected in a detachable manner to the container (18), and with which the fluid can be pumped out of the container (18) and delivered, comprises a monitoring unit (54), with which device-related and/or user-related data can be collected and stored, and a display (76) interacting with the monitoring unit (54) for entering and displaying the user-related data and/or the device-related data. The invention also relates to a system for monitoring such a device (10₂).

14 Claims, 8 Drawing Sheets

(52) U.S. Cl.
CPC .............. *A61L 2/26* (2013.01); *A61L 2202/14* (2013.01); *A61L 2202/15* (2013.01)

(58) Field of Classification Search
CPC ...... A47K 5/1217; A47K 5/14; A47K 5/1205; G08B 17/06; G08B 21/245
See application file for complete search history.

(56) References Cited

U.S. PATENT DOCUMENTS

| | | |
|---|---|---|
| 2015/0199883 A1 | 7/2015 | Hartley et al. |
| 2018/9036467 | 12/2018 | Kamatchi |

OTHER PUBLICATIONS

Office action dated Apr. 26, 2021, in corresponding German application No. 10 2020 122 427.3.

DEVICE FOR DELIVERING A FLUID, IN PARTICULAR A CLEANING, CARE OR DISINFECTING FLUID FOR HANDS AND A SYSTEM FOR MONITORING SUCH A DEVICE

The present invention relates to a device for delivering a fluid, in particular a cleaning, care or disinfecting fluid for hands. Furthermore, the invention relates to a system for monitoring such a device.

Such devices are known, for example, from EP 3 650 128 A1 and DE 10 58 272 A1 and are used in a variety of ways. For example, in craft businesses in which the craftsmen regularly soil their hands, such devices are used to deliver a cleaning fluid, in particular soap, in order to be able to clean their hands. However, since frequent hand washing is a burden for the skin in the area of the hands, such devices are also used to deliver care products, for example in the form of hand cream. This can prevent skin diseases. The use of such care products may even be mandatory for certain establishments.

Another very important field of application of such devices is found in facilities in the health sector, in particular in hospitals, retirement homes and medical practices. In these facilities, the devices for delivering disinfecting fluids are used to reduce the spread of pathogens such as bacteria and viruses.

Such devices have a pump and metering unit, which in many cases has to be operated with one hand. The released fluid is collected with the other hand in order to then massage it into the skin in the area of the hands using both hands. However, due to the fact that the devices are used by a large number of persons, there is a risk of the transfer of pathogens due to the contact with the device which is necessary to operate the pump and metering unit. Therefore, devices are known in which the pump and metering unit can be driven by means of a drive unit that can be triggered in a contactless manner, so that no contact with the device is necessary. This significantly reduces the risk of the transfer of pathogens. However, such devices cannot guarantee that people who are obliged to disinfect their hands by guidelines will in fact disinfect their hands as prescribed. In addition, it is not possible to document the hand disinfection carried out.

The object of an embodiment of the present invention is to specify a device for delivering a fluid, in particular a cleaning, care or disinfecting fluid for hands, which is able to document the disinfection processes carried out. In addition, a development of the invention is based on the object of creating a system in which the device can be integrated for data exchange.

The object is achieved with the features specified in claims 1 and 15. Advantageous further developments are the subject of the dependent claims.

An embodiment of the invention relates to a device for delivering a fluid, in particular a cleaning, care or disinfecting fluid for hands, comprising
- a housing, which
  - encloses a cavity in which a container for holding the fluid can be installed, and
  - forms an outer housing surface,
- a pump and metering unit,
  - which can be connected or is connected to the housing,
  - which can be connected to the container in a detachable manner, and
  - with which the fluid can be pumped out of the container and delivered,
- a monitoring unit with which device-related and/or user-related data can be collected and stored, and
- a display interacting with the monitoring unit for entering and displaying the user-related data and/or the device-related data.

The monitoring unit controls or regulates all processes which the device carries out. By means of the monitoring unit, for example, it is possible to detect when a delivery of fluid from the device has taken place. This information is an example of device-related data. In addition, user-related data that can be assigned to a delivery process can be entered by means of the display. In this way, the delivery process can be assigned to a specific user of the device. This assignment can be stored in the monitoring unit and read out for documentation purposes via a corresponding interface. It is thus possible to provide evidence as to whether a particular person has actually carried out the prescribed hand disinfection, for example.

In this case, the device can be equipped with a drive unit which interacts with the monitoring unit and by means of which the pump and metering unit can be driven. In this case, the delivery of the fluid can be carried out without the manual actuation of an actuating lever. In addition, the monitoring unit can specify and record the amount of fluid to be delivered.

According to a further embodiment, at least one ultrasonic sensor can be arranged on the outer housing surface. The ultrasonic sensor can be arranged on the housing surface in such a way that the ultrasonic waves emitted by it can reach the hands of a user in a position that is convenient for the user. The ultrasonic sensor can detect whether the user is wearing jewelry or other metallic objects on his hands that could interfere with hand disinfection and therefore must not be worn in accordance with many regulations during certain activities. In the event that the user is wearing one or more metallic objects on his hands, the device can issue a warning signal, for example in optical form, which is indicated on the display. The actual delivery process of the fluid is only enabled when the ultrasonic sensor does not detect any metallic objects and consequently an OK message is present. Thus, hand disinfection in accordance with regulations can be ensured.

In a further embodiment, a number of light sources which emit ultraviolet radiation can be arranged on the outer housing surface. For example, fluorescent additives can be added to the fluid, which become visible to the user in interaction with the ultraviolet radiation. If the user holds his hands under the light sources, the user can determine whether the entire hand surface has been wetted by the fluid which has been delivered from the device or whether there are places which have not been reached by the fluid. In the latter case, the user can request additional fluid from the device and apply the additional fluid to the not yet wetted areas. This increases the quality of hand disinfection and reduces the risk of spreading pathogens.

In a further embodiment, the device can comprise at least one UV sensor for registering the ultraviolet rays reflected by the hands of a user. While, in the event that the device does not have a UV sensor (sensor for detecting ultraviolet radiation), the control of whether or not the fluid delivered by the device has wetted the entire hand surface is subject to the user himself, this control can be automated by means of the UV sensor, for which purpose a corresponding evaluation software is stored on the monitoring unit. The quality of hand disinfection is thereby increased. In addition, it can be automatically determined whether the relevant regulations have been complied with or not.

In a further embodiment, at least one first camera can be arranged on the outer housing surface. The first camera can be used alternatively to or cumulatively with the UV sensor. The first camera can also be used to check whether the hand surface has been completely wetted by the fluid. For this purpose, a corresponding image processing software is stored on the monitoring unit. The camera can be used alternatively to or cumulatively with the ultrasonic sensor. The image processing software can be set in such a way that it is able to recognize, for example, jewelry or artificial nails and generate corresponding warning signals. The quality of hand disinfection is thereby increased. In addition, it can be automatically determined whether the relevant regulations have been complied with or not.

A further embodiment can be distinguished in that the device has a user identification device with which the identity of the user of the device can be established. As already mentioned, for documentation purposes and to prove whether a particular user has carried out the prescribed hand disinfection, it is necessary to assign a specific delivery process of the fluid to a user of the device in question. This can be done by means of an input using the display. However, the determination of the identity of the user can be simplified and shortened by means of the user identification device. In addition, the user identification device can be designed in such a way that contact with the display, for example, is not necessary, as a result of which the transmission of pathogens is counteracted.

In accordance with a further embodiment, the user identification device can have a readout unit for reading out an RFID transponder. RFID transponders are very handy and can be carried, for example, on the key fob or on a wristband. RFID transponders are often used for access control, and therefore employees of a hospital, for example, carry such RFID transponders anyway. One only has to hold the RFID transponder against the readout unit in order to be able to determine the identity of the user, which is a very quick and easy process to perform.

In a further embodiment, it may be appropriate for the user identification device to comprise a second camera. Unlike RFID transponders, the second camera checks a user's biometric features, such as the facial features or the pattern of the iris. While RFID transponders can be exchanged between several users and thus a manipulation of the identity of the user is possible, manipulation in the use of biometric features is at least significantly more difficult.

In a further embodiment, the readout unit and/or the second camera can be arranged in the display. As a result, the assembly outlay of the device can be reduced, since in particular the cabling is simplified compared to an embodiment in which the readout unit and the second camera are arranged outside the display. Since the user will intuitively orientate himself toward the display, a long search for the readout unit or the second camera is avoided, as a result of which the length of stay at the device is also reduced for users who are using the device for the first time or only use it very rarely, for example visitors.

In a further embodiment, a number of keypads can be arranged in the display, each keypad being assigned to a specific activity related to a disinfection process. For example, in a hospital, the regulations in force there may prescribe different standards for hand disinfection. For example, hygienic hand disinfection is different from surgical hand disinfection. Thus, for one activity, hygienic hand disinfection can be prescribed, for example for a catheter change, and for another activity, for example a surgical procedure, surgical hand disinfection can be prescribed. The amount of fluid delivered by the device can differ from a hygienic hand disinfection.

Consequently, a user who wants to perform a certain activity can select a keypad assigned to this activity and then carry out the hand disinfection. The amount of fluid delivered by the device may differ depending on the activity. The monitoring unit can be configured accordingly. It can thus be ensured that the appropriate amount of the fluid is delivered for the hand disinfection in question, thereby avoiding overdosing and under-dosing. At the same time, it can be understood which activity which person carried out with the appropriate hand disinfection and when. This makes it particularly easy to meet and document compliance regulations.

In a further embodiment, the device can comprise a transmitting and receiving unit for data exchange with external units. As mentioned, device-related and/or user-related data can be stored with the monitoring unit. In order to process these data further, however, the monitoring unit must be read out. For this purpose, for example, a suitably set-up readout device can be used, which must be connected to the device. In the present embodiment, however, the device comprises a transmitting and receiving unit, by means of which the stored data can be transmitted wirelessly, for example via Bluetooth or WLAN, to an external unit. The data exchange can take place at regular intervals or quasi-continuously. In the latter case, the state of the device can be determined almost in real time. Extraordinary events which require certain measures can thus be initiated in a timely manner, as a result of which a prolonged device downtime is prevented.

A further embodiment can be characterized by the fact that the device comprises
  a level sensor for determining the level of the fluid in the cavity and/or
  a temperature sensor for determining the temperature of the fluid in the cavity.

The determination of the fill level makes it possible to generate a corresponding signal when the fill level falls below a certain level. As a result, the replacement of the container with a full container can be initiated in good time, preventing the container from being empty and the device being used not as intended.

Normally, it can be assumed that the fluid in the container has approximately the same temperature as the environment of the device. However, if the temperature of the fluid rises, this may indicate contamination of the fluid, as a result of which the fluid can no longer fulfill its intended purpose and has to be replaced. In this respect, this makes it possible to make a significant contribution to avoiding the spread of pathogens. In addition, the temperature sensor can also be used to detect sources of fire and determine their position. The increase in the temperature of the fluid as a result of contamination is significantly slower than an increase in temperature as a result of a fire, and the rise in temperature in the case of a fire is significantly more pronounced than in the course of contamination. A distinction between a fire and contamination is therefore possible with sufficient certainty.

In accordance with a further embodiment, the drive unit can be activated by means of a motion sensor that can be triggered in a contactless manner and the motion sensor can be designed as an ultrasonic sensor or as a proximity sensor. Motion sensors that are usually used for devices of the present type are designed in the manner of light barriers. However, it may be the case that reliable actuation of the drive unit is no longer possible under unfavorable lighting conditions. The use of an ultrasonic sensor increases the reliability of the activation of the drive unit. However, proximity sensors can also be designed in such a way that they trigger reliably in unfavorable light conditions, in particular if they are designed as inductive or capacitive proximity sensors.

In a further embodiment, it may be appropriate for the outer housing surface to be designed as an antibacterial surface and/or as a superhydrophobic surface and/or as a superamphiphobic surface. The growth of microorganisms such as bacteria and fungal cultures poses a hygiene risk. Many of the microorganisms are pathogens. An antibacterial surface prevents the growth of microorganisms. An antibacterial surface can be provided, for example, with a coating applied to the housing surface. This coating may contain additives which are highly effective against microorganisms but harmless to the human organism. However, these additives do not necessarily have to be contained in a coating applied to the housing surface, but can alternatively be added to the material from which the housing is manufactured. It is also possible to manufacture the complete housing from an antibacterial material.

The superhydrophobic surface prevents the attachment of microorganisms, in particular of pathogens, which significantly reduces the risk of spreading pathogens when using the device according to the proposal. The property whereby pathogens and other particles are prevented from attaching to the superhydrophobic surfaces is often also called the lotus effect. The superhydrophobic surface can be provided with a coating applied to the housing surface. This coating may also contain the above-mentioned antibacterial additives. A superamphiphobic surface is both water and oil repellent and can also be applied as a coating to the housing surface.

A design of the invention relates to a system for monitoring a device according to one of the previous embodiments, comprising
 a device according to one of the previous embodiments,
 a first external unit on which user-related data are stored, which can be read out by means of the transmitting and receiving unit, and
 a second external unit, on which the user-related data and device-related data can be deposited and evaluated, the second external unit having a second transmitting and receiving unit for data exchange with the transmitting and receiving unit of the device.

The technical effects and advantages which can be achieved with the proposed system correspond to those which have been discussed for the relevant embodiment of the device. In summary, it should be noted that data exchange is possible in a simple manner. The data stored on the monitoring unit can be evaluated by means of the second external unit. Thus, for example, it is possible to determine who used the device and when. This in turn makes it possible to determine whether the person concerned has complied with certain regulations or not. It is therefore possible to realize extensive documentation with regard to the use of the device. In addition, it can also be determined and documented if, for example, the temperature of the fluid has exceeded a certain value or the fill level of the fluid has fallen below a certain value. Suitable countermeasures can thus be initiated in a timely manner and a device downtime can be avoided or kept low.

Furthermore, the system can be operated in such a way that access to an operating room, for example, is only enabled if a person who is authorized to access in principle has disinfected his hands according to the regulations. To this end, the system can interact with a door opener which, in the case of hand disinfection according to the regulations, is activated and opens the door in question.

In a further design, it can be provided that the second transmitting and receiving unit is set up in such a way that a data exchange with a third external unit is made possible. The second external unit can be, for example, a server of a hospital, a doctor's office or a business. The third external unit may be a parent server where data from many second external units converge. This allows infection chains to be traced and the relevant users to be informed accordingly. For example, if it has been found that a person has been infected with a particular pathogen and that person has used one of the proposed devices, a corresponding warning may be sent to the persons who have used the device shortly thereafter. These people can then take appropriate countermeasures such as quarantine or the like. In addition, the device in question can be subjected to a thorough disinfection, for example by autoclaving or cleaning in a dishwasher. The plastics used have sufficient resistance to the conditions prevailing during cleaning in a dishwasher or autoclave. This can also counteract the spread of pathogens.

Exemplary embodiments of the invention are explained in more detail below with reference to the accompanying drawings. In the drawings.

Figure 1:
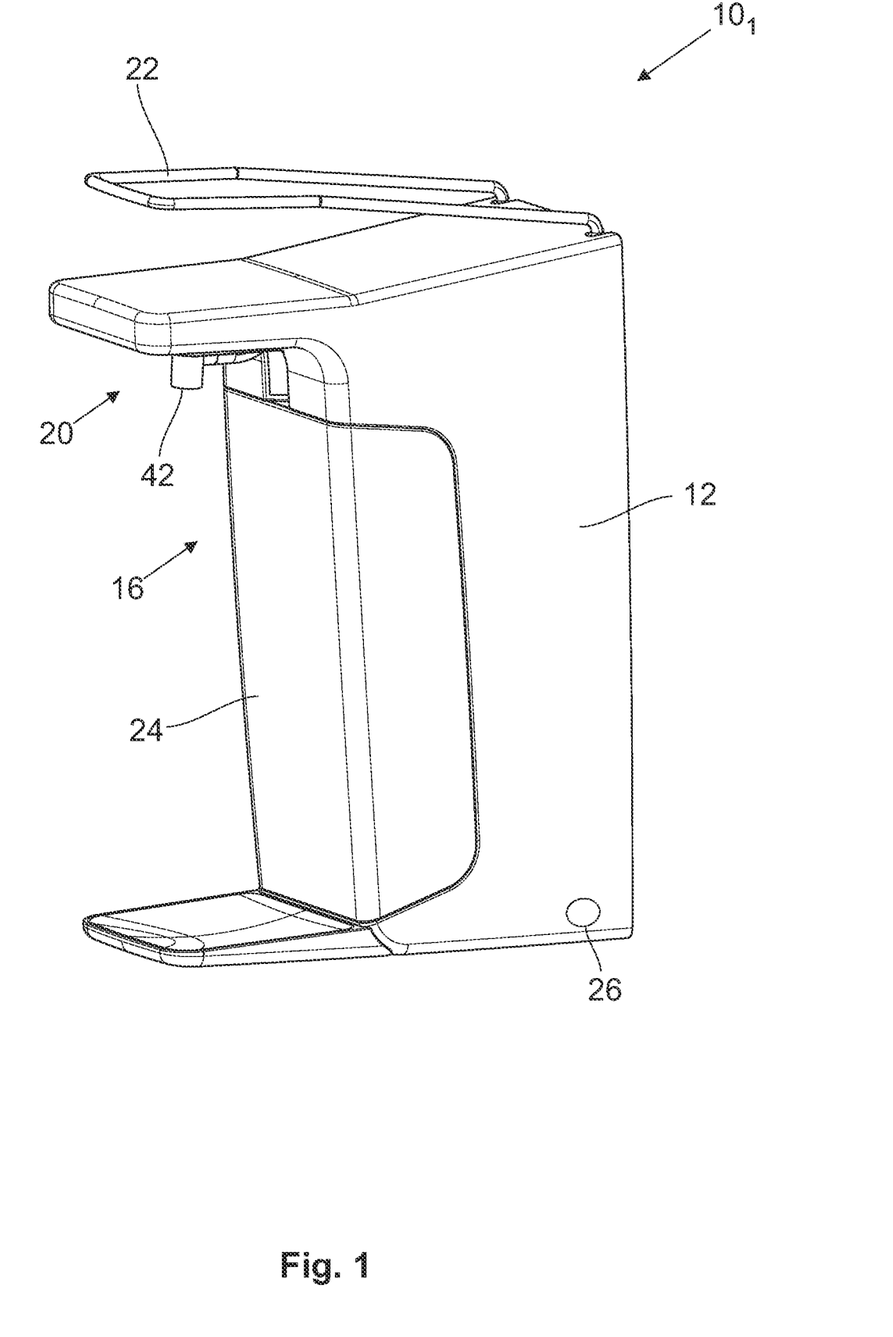
FIG. 1 shows a perspective view of a first embodiment of a device according to the proposal for delivering a fluid, in particular a cleaning, care or disinfecting fluid for hands, with a closure body.
Figure 3A:
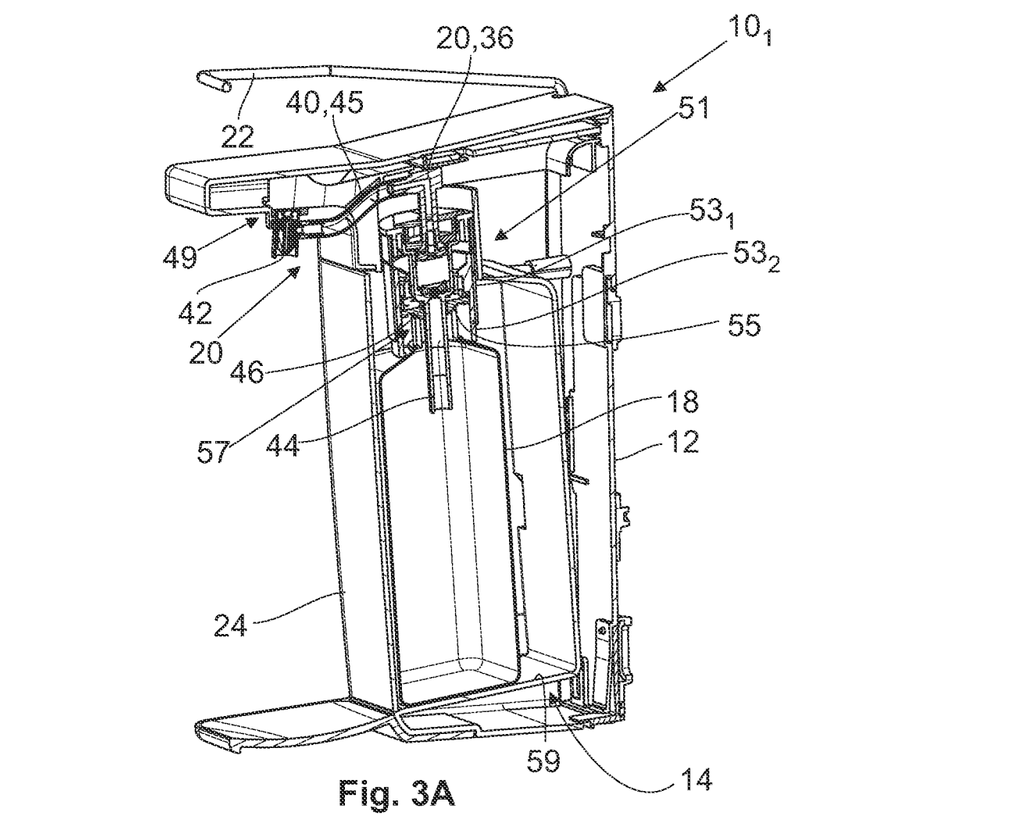
FIG. 3A shows a perspective sectional representation through the device shown in FIG. 1.

FIG. 1 shows a perspective view of a first embodiment of a device $10_1$ according to the proposal for delivering a fluid, in particular a cleaning, care or disinfecting fluid for hands. The device $10_1$ comprises a housing 12, which encloses a cavity 14 (see FIG. 3A). The housing 12 forms an opening 16 through which the cavity 14 is accessible. As can be seen in FIG. 3A, a container 18, in which a fluid, for example a cleaning fluid, a care fluid or a disinfecting fluid, can be stored, can be introduced into the cavity 14 and connected by means of a thread or a bayonet closure (not shown), for example, to a pump and metering unit 20, which will be described in more detail below. FIG. 1 shows an actuating lever 22 of the pump and metering unit 20, which lever is fastened to the housing 12 in a rotatable manner.

Figure 2:
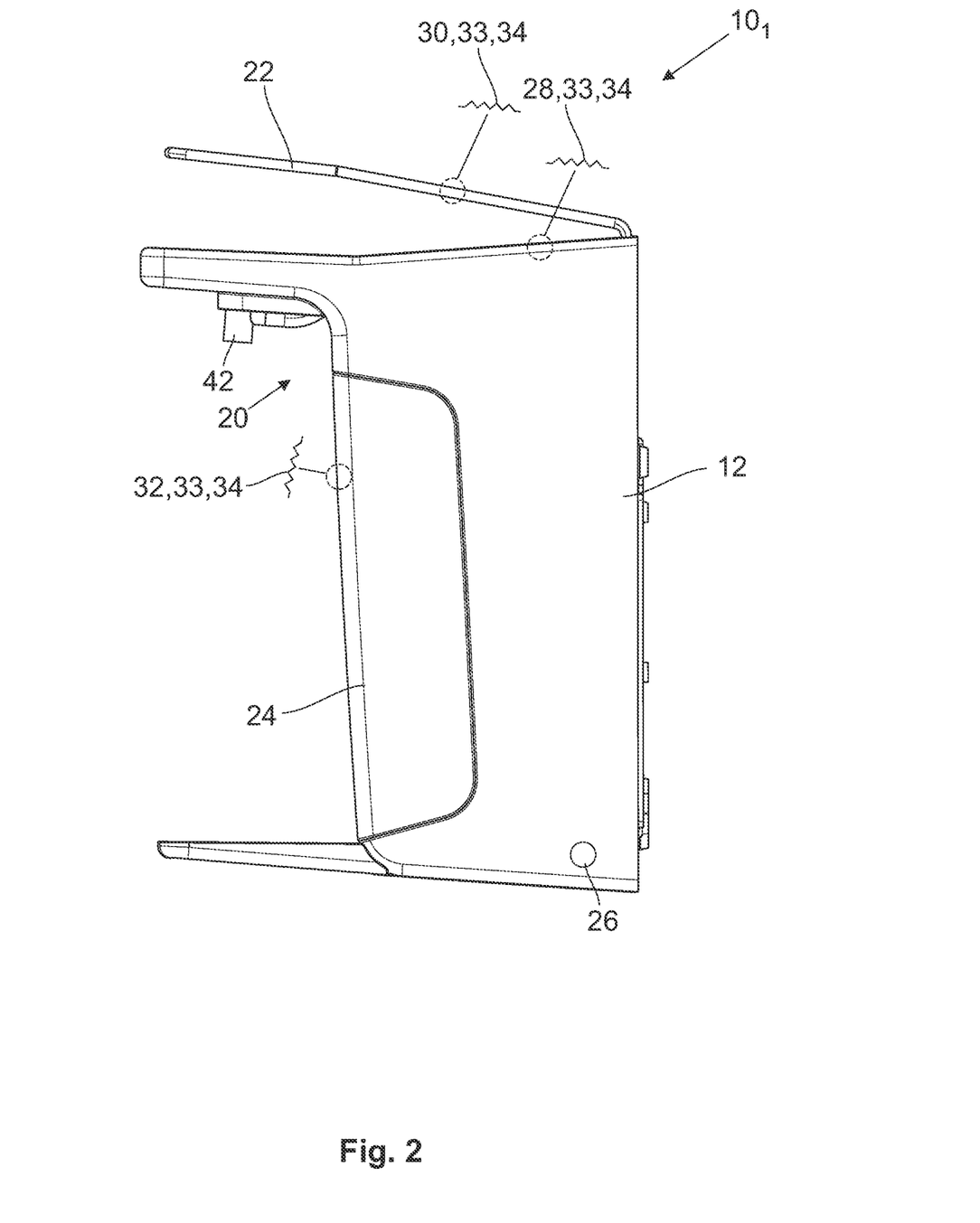
FIG. 2 shows the device shown in FIG. 1 on the basis of a side view with a closure body.

In FIG. 2, the device $10_1$ shown in FIG. 1 is shown on the basis of a side view. It can be seen both from FIG. 1 and from FIG. 2 that the opening 16 is closed by means of a closure body 24, which is why the container 18 cannot be seen in FIGS. 1 and 2. However, it may be prescribed that the container 18 is visible from the outside. In this case, the closure body 24 can be made of a transparent material. The closure body 24 can be locked to the housing 12 by means of a plug connection. In order to release it from the housing 12, the closure body 24 must be somewhat compressed by a user. Not shown is an embodiment in which the closure body 24 is movably fastened to the housing 12 between a closed position and an open position. To this end, the housing 12 can have a receiving opening 26, wherein details of the attachment are not shown for reasons of representation.

The housing 12 forms an outer housing surface 28 (see FIG. 2). Accordingly, the pump and metering unit 20 forms a pump and metering unit outer surface 30 and the closure body 24 forms a closure body outer surface 32. In the illustrated embodiment, the pump and metering unit outer surface 30 is formed by the above-mentioned actuating lever 22 of the pump and metering unit 20. The outer housing surface 28, the pump and metering unit outer surface 30 and the closure body outer surface 32 are each designed as an antibacterial surface 33 and as a superhydrophobic surface 34, which are shown symbolically and enlarged in FIG. 2. The antibacterial surface 33 prevents the growth of microorganisms and the superhydrophobic surface 34 prevents the attachment of particles, in particular of pathogens, as a result of which the spread of pathogens and the diseases caused by them can be counteracted. Alternatively, the actuating lever 22 can be made of stainless steel without it having a coating.

As can be seen from FIG. 2, the closure body outer surface 32 closes with the outer housing surface 28 in an offset-free manner when the closure body 24 is connected to the housing 12. This avoids the formation of dead spaces in which pathogens could accumulate and multiply.

FIG. 3A shows a perspective sectional representation through the device $10_1$ shown in FIGS. 1 and 2. In order to illustrate the construction of the pump and metering unit 20, this is shown separately in FIG. 3B in a slightly different embodiment, the functions described below being the same in both embodiments.

Figure 3B:
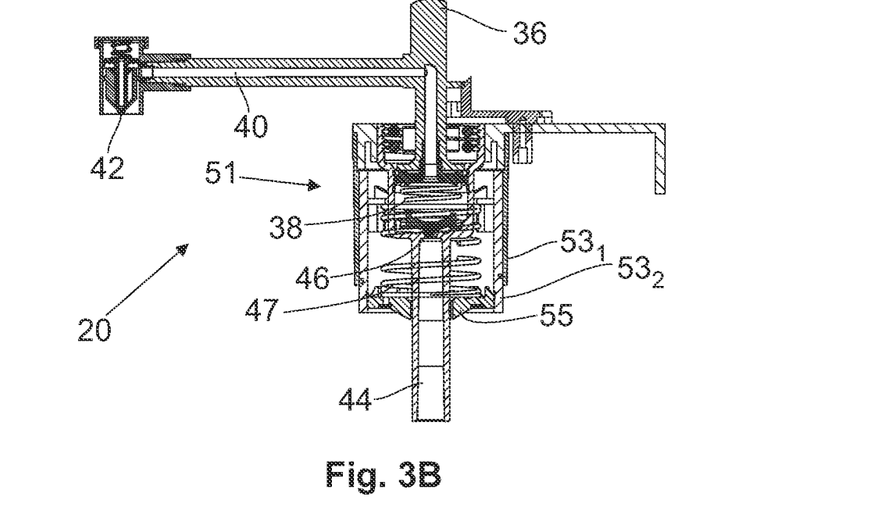
FIG. 3B shows an isolated representation of a pump and metering unit.

It can be seen that the pump and metering unit 20 has a pump plunger 36, which can be pressed into the cavity 14 of the housing 12 by means of the actuating lever 22, the pump plunger 36 being preloaded with a first spring 38. The pump plunger 36 comprises a channel 40, which at its free end forms a delivery opening 42, which can be designed as a foam nozzle. At its closed end, the channel 40 opens into a suction tube 44, which protrudes into the container 18 when the container 18 is connected to the pump and metering unit 20. An extension hose (not shown) which extends to the base of the container 18 can be connected to the suction tube 44. Between the delivery opening 42 and the head of the pump plunger 36, the channel 40 is formed by a flexible hose 45 in the embodiment shown in FIG. 3A, so that relative movements between the pump plunger 36 and the delivery opening 42 can be compensated. In addition, the pump and metering unit 20 is provided with a non-return valve 46, which is preloaded with the first spring 38 into a closed position, as shown in FIGS. 3A and 3B.

When a user presses the actuating lever 22, the pump plunger 36 is displaced into the cavity 14 of the housing 12, the first spring 38 being compressed. The non-return valve 46 remains in the closed position. Due to the reduction of the volume between the delivery opening 42 and the non-return valve 46, the fluid exits through the delivery opening 42, provided that the channel 40 between the non-return valve 46 and the delivery opening 42 is completely filled with fluid.

If the user lets go of the actuating lever 22, the pump plunger 36, together with the actuating lever 22, is returned to the starting position by the first spring 38. Due to the increase in the volume between the non-return valve 46 and the delivery opening 42, the non-return valve 46 is opened and the fluid is sucked out of the container 18 into the suction tube 44. In order to prevent already delivered fluid or air from the environment from being sucked back into the channel 40 through the delivery opening 42, a non-return valve function is integrated in the delivery opening 42.

FIG. 3A also shows that the pump and metering unit 30 is connected to the housing 12 in a detachable manner by means of a fastening device 49. In particular in the area of the delivery opening 42, it can be seen that the fastening device 49 has groove-shaped sections into which the pump and metering unit 30 can be inserted with a translational movement perpendicular to the section plane of FIG. 3A and removed from it again.

Furthermore, the pump and metering unit 30 has an adapter unit 51 which, in the present embodiment, comprises a first tubular section $53_1$ and a second tubular section $53_2$ which engage one another and are fastened to one another by means of a thread (see in particular FIG. 3B). By turning, the second tubular section $53_2$ can be inserted more or less far into the first tubular section $53_1$, as a result of which the second tubular section $53_2$ protrudes more or less far from the first tubular section $53_1$. In the second tubular section $53_2$, a sealing body 55 is mounted so as to be axially movable, the sealing body 55 being preloaded with a second spring 47 into the position shown in FIG. 3B.

To insert the container 18, it is pressed against the sealing body 55 with an opening 57 and placed with the bottom on an inclined contact surface 59 (see FIG. 3A). Depending on the size of the container 18, the sealing body 55 is shifted more or less far toward the non-return valve 46, the second spring 47 being compressed. As a result, on the one hand, containers 18 can be used which differ in their height within certain limits. On the other hand, it is ensured that a sufficiently large contact pressure acts between the sealing body 55 and the opening 57 of the container 18 in order to seal the container 18 with respect to the pump and metering unit 20.

If the height difference between two containers 18 exceeds the distance that the sealing body 55 can travel within the tubular section $53_2$, the second tubular section $53_2$ can be moved further out of or into the first tubular section $53_1$ by turning. The aim is to ensure that the free end of the second tubular section $53_2$ comes into contact with the container 18 in order to protect the opening 57 of the container 18 from the penetration of dirt.

Figure 4:
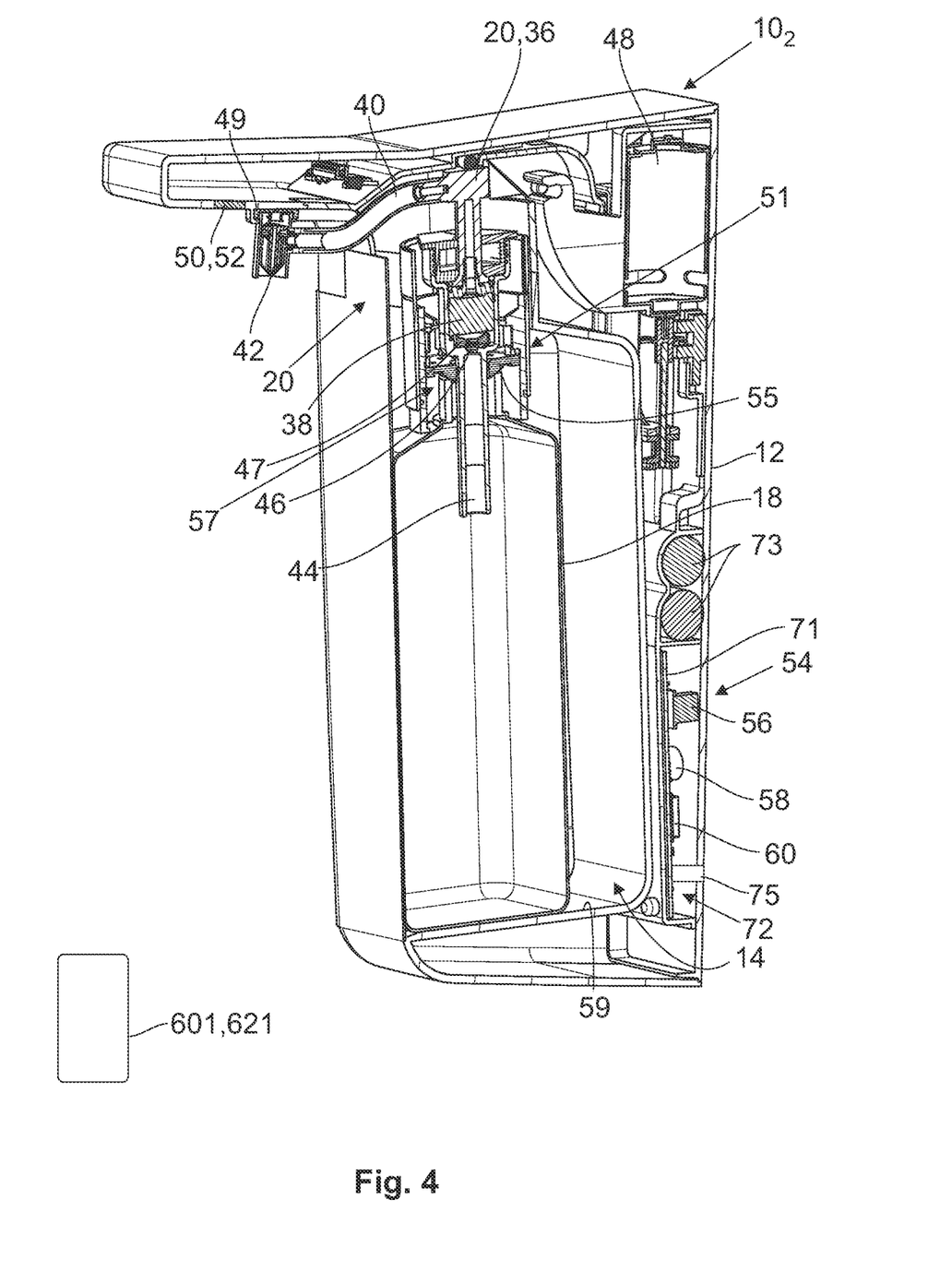
FIG. 4 shows a perspective sectional representation through a second embodiment of the device according to the proposal in a first configuration.
Figure 5:
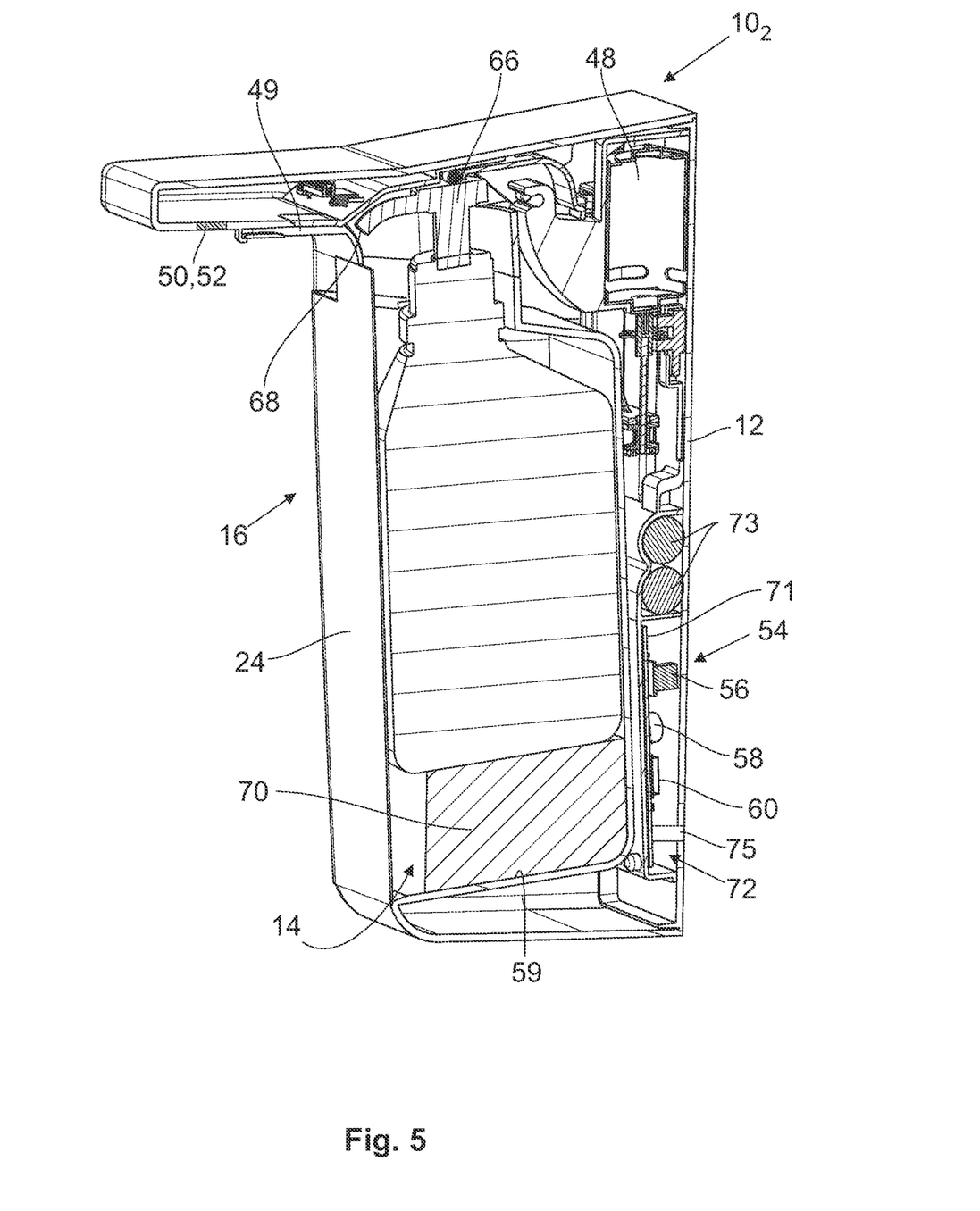
FIG. 5 shows a perspective sectional representation through the second embodiment of the device according to the proposal in a second configuration.

FIG. 4 shows a second embodiment of the device $10_2$ on the basis of a perspective sectional representation which is based on the representation of FIG. 3. The device $10_2$ is in a first configuration. FIG. 5 shows the second embodiment of the device $10_2$ also on the basis of a perspective sectional representation, wherein the device $10_2$ is in a second configuration. The two configurations will be discussed later.

FIG. 4 shows that the device $10_2$ is equipped with a drive unit 48, with which the pump plunger 36 can be moved independently into the cavity 14 and which can be designed, for example, as an electric motor. In this case, it is not necessary for the user to press the actuating lever 22 with his hand. Consequently, according to the second embodiment, the device $10_2$ has no actuating lever 22.

To activate the drive unit 48, the device $10_2$ comprises a motion sensor 50, which in the present exemplary embodiment is designed as an ultrasonic sensor 52 or a proximity sensor 52. The proximity sensor 50 is shown only in principle in FIG. 4 and is arranged on a sensor board, not shown in any more detail here, which is arranged in the cavity above the proximity sensor 50 of the device 10₂. The user must insert his hand into the detection area of the motion sensor 50 without, however, having to touch the device 10₂. As a result, a signal is generated by the motion sensor 50 and transmitted to the drive unit 48. The drive unit is activated and a certain amount of fluid is delivered via the delivery opening 42. The mode of action of the pump and metering unit 20 corresponds to that described for the first embodiment of the device 10₁, with the essential difference that the movement of the pump plunger 36 is effected by the drive unit 48 and not as a result of the movement of the actuating lever 22.

Since the device 10₂ can be activated in a contactless manner according to the second embodiment, there is a risk that particles, in particular pathogens, which have accumulated on the pump and metering unit outer surface 30, can accumulate on the hand of the user and thereby get into the body of the user.

As can also be seen from FIG. 4, the device 10₂ is equipped with a monitoring unit 54, with which device-related and/or user-related data can be collected and stored. The monitoring unit 54 comprises a circuit board 71, which is arranged in a further cavity 72 enclosed by the housing 12. In FIG. 4 it can also be seen that the device 102 has a level sensor 56 arranged on the circuit board 71, with which the fill level of the fluid in the container 18 can be determined. In addition, the device 10₂ is equipped with a temperature sensor 58, which is also arranged on the circuit board 71 and with which the temperature in the environment of the temperature sensor 58 can be determined. The temperature sensor 58 is arranged such that it substantially determines the temperature of the fluid in the container 18. However, if the temperature in the environment of the device 101 drops or increases significantly, as may be the case, for example, in the case of a fire, the temperature sensor 58 will also detect this temperature change.

Both the level sensor 56 and the temperature sensor 58 cooperate with the monitoring unit 54 and supply at least some of the above-mentioned device-related data.

FIG. 4 also shows that the device 10₂ also has a transmitting and receiving unit 60, which is also arranged on the circuit board 71. With this transmitting and receiving unit 60, data deposited on the monitoring unit 54 can be exchanged with external units 62. A first external unit 62₁ is shown in FIG. 4, which can be designed, for example, as a smartphone, as a transponder, as a barcode or the like. As a result, a user who uses the device 10₂ can be identified. Thus, it is possible, for example, to be able to activate the drive unit 48 only when a user has previously been able to be recognized as an authorized user.

FIG. 4 further shows that the device 10₂ comprises two batteries 73, with which the supply of the drive unit 48 and the electronic components such as the temperature sensor 58 with electrical energy can be ensured. As mentioned, the device 10₂ has a transmitting and receiving unit 60, with which data can be exchanged wirelessly with external units 62₁. In addition, the device 10₂ also has an Ethernet connection 75, with which the device 10₂ can be connected to a LAN in a wired manner With a corresponding configuration of the LAN, the electronic components can also be supplied with electrical energy via the LAN (Power over Ethernet).

As mentioned, the proximity sensor 50 is mounted on its own sensor board, not shown in FIGS. 4 and 5. The provision of the sensor board, which is spatially separated from the circuit board 71, makes it possible in a simple manner to provide an embodiment of the device 10₂, which on the one hand can be activated without contact using the proximity sensor 50, but on the other hand does not have the circuit board 71 and consequently the sensors mounted thereon, for example, the temperature sensor 58. Such an embodiment of the device 10₂ can be useful if documentation is not necessary.

As mentioned, FIG. 5 shows the device 10₂ in a second configuration. If we compare FIGS. 4 and 5, it is found that the pump and metering unit 20 has been removed from the housing 12 in the second configuration and another container 18 has been inserted into the cavity 14. This container 18 has its own pump and metering unit 66, which in this case is non-detachably connected to the container. This pump and metering unit 66 also comprises its own delivery opening 68.

The container 18, which is inserted into the cavity 14 in FIG. 5, also has a significantly lower height than the container which has been inserted into the cavity in FIG. 4. In order to ensure that the pump and metering unit 66 can interact with the drive unit 48 and that the delivery opening 68 is arranged in such a way that the delivered fluid can also leave the cavity 14, a support body 70 is placed on the contact surface 59, on which the container 18 is supported. Alternatively, the support body can also be hooked into the housing 12. This compensates for the lower height of the container 18.

Figure 6:
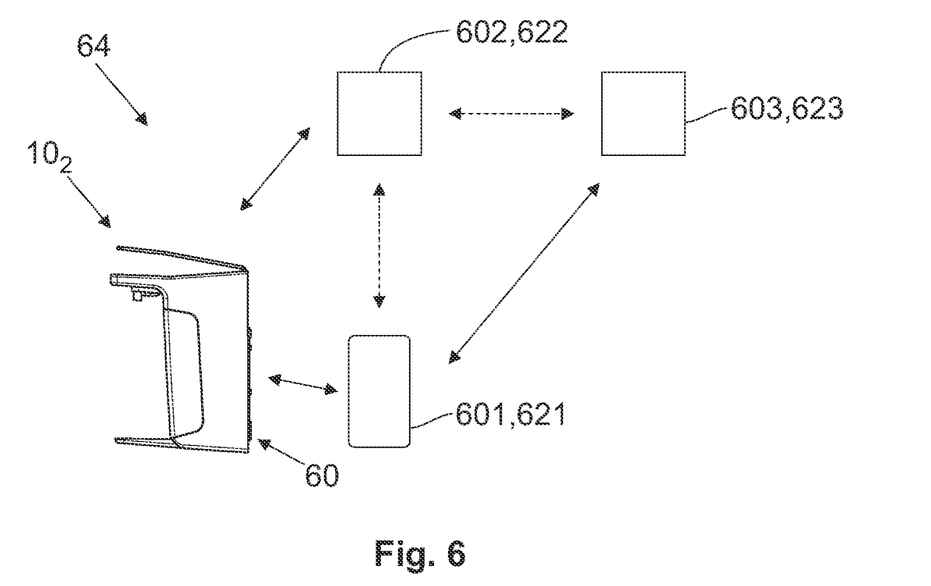
FIG. 6 shows a basic representation of a system for monitoring the device shown in FIGS. 1 to 3.

In the following, reference is made to FIG. 6, in which a system 64 for monitoring the device 10₂ shown in FIGS. 4 and 5 is shown on the basis of a basic representation. The system 64 comprises the device 10₂, the above-mentioned first external unit 62₁, a second external unit 62₂ and a third external unit 62₃, the third external unit 62₃ being only optional. The number of devices 10₂, first external units 62₁, second external units 62₂ and third external units 62₃ can be selected as desired.

As mentioned, the first external unit 62₁ can be designed as a barcode which can be read out by the transmitting and receiving unit 60 of the device 10₁. Consequently, it is not necessarily necessary for the first external unit 62₁ to have a first transmitting and receiving unit 60₁, wherein this is the case, for example, when the first external unit 62₁ is designed as a smartphone or as a transponder.

The second external unit 62₂ can be, for example, a server of a hospital, a doctor's office or a factory, which can communicate with the device 10₂ via a WLAN network, for example, and consequently has a second transmitting and receiving unit 60₂. The second external unit 62₂ can exchange data with the third external unit 62₃, which can also be designed as a server which communicates with a plurality of second external units 62₂ using a third transmitting and receiving unit 60₃. Depending on the configuration of the first external unit 62₁, the second external unit 62₂ and the third external unit 62₃, the third external unit 63₃ can also communicate with the first external unit 62₁.

The system 64 can be operated, for example, in the following ways: As mentioned, the fill level of the fluid in the container 18 can be monitored by means of the level sensor 56, and the temperature of the fluid in the container 18 and the temperature in the immediate vicinity of the device 10₁ by means of the temperature sensor 58. In the event that the fill level of the fluid in the container 18 falls below a certain value, a corresponding signal can be generated by the second external unit 62₂ and transmitted to a specific person. This person can, for example, be the owner of the first external unit 62₁, which is designed as a smartphone. This person can now initiate the replacement of the container, so as to avoid the container 18 located in the device $10_2$ being completely emptied and thus the device $10_2$ being used not as intended.

If the temperature detected by the temperature sensor 58 rises to a certain value over a certain period of time, this can be an indication of contamination of the fluid. Again, the second external unit $62_2$ generates a corresponding signal and sends it to the first external unit $62_1$, so that the responsible person can also initiate the replacement of the container located in the device $10_2$. If the temperature measured by the temperature sensor 58 rises to an unusually high value within a very short time, this can be interpreted as an indication of a fire. The second external unit $62_2$ can now trigger a fire alarm. Since the location of the device $10_2$ whose temperature sensor 58 has registered the temperature rise is known, the source of the fire can be located.

Due to the fact that personal data are exchanged with the device $10_2$ with the first external unit, it is possible to determine which persons used the device $10_2$ at what point in time. The corresponding information is transmitted to the second external unit $62_2$, where appropriate documentation is carried out, which can be transmitted, for example, to the health department or the professional association. In the event that the person concerned has not used the device $10_2$ as intended, a corresponding notification can be issued to that person.

In the event that it is determined that a person has become infected with a certain pathogen, this information is stored in the third external unit $62_3$. If the person has used the device $10_2$ before the time at which the infection has been detected, a corresponding signal can be generated which indicates the need to disinfect the device $10_2$ as quickly as possible, for example by autoclave. Furthermore, other persons who have used the device $10_2$ shortly after the infected person can be informed in order to be able to initiate appropriate countermeasures.

Figure 7:
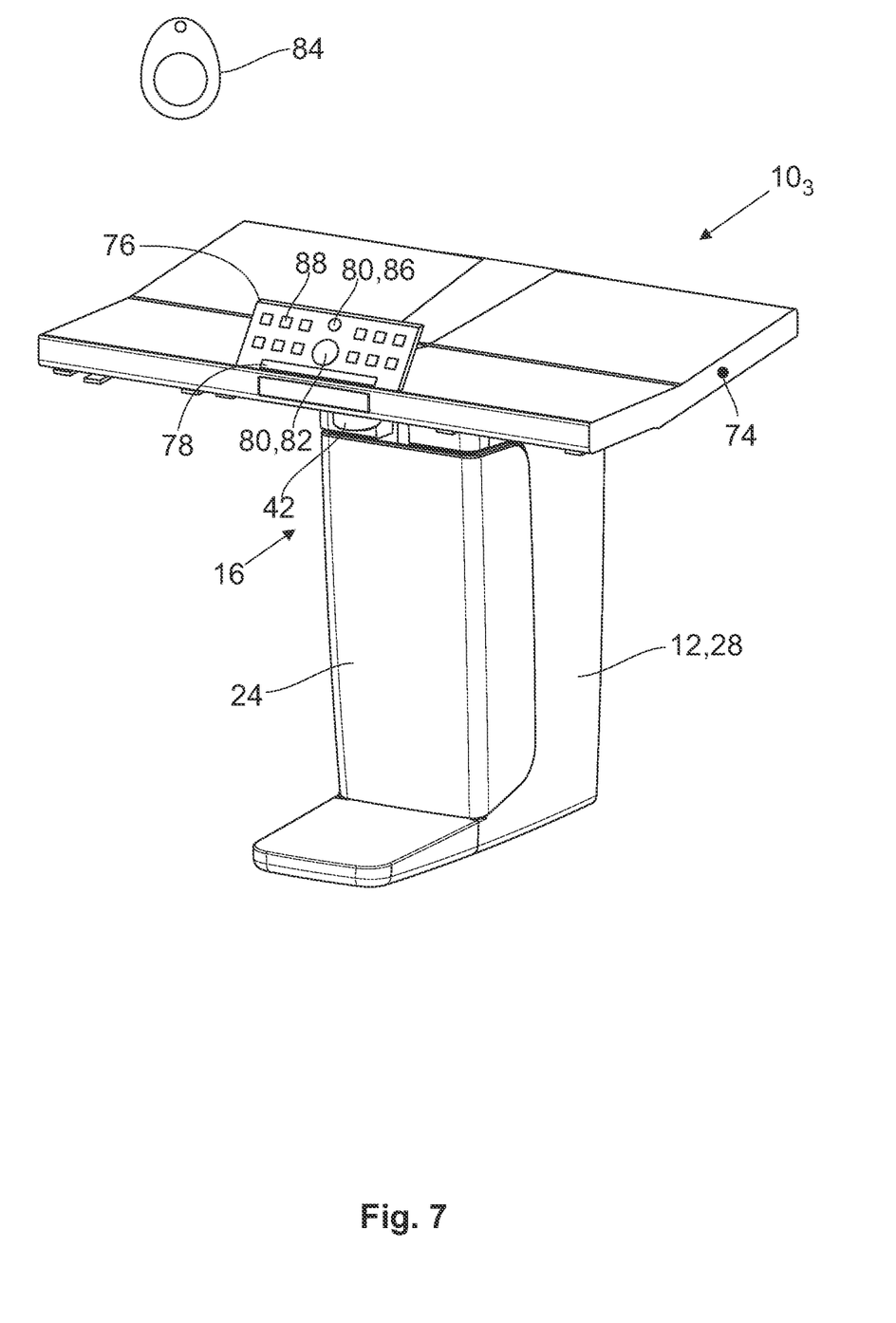
FIG. 7 shows a first perspective representation of a third embodiment of the device according to the proposal.
Figure 8:
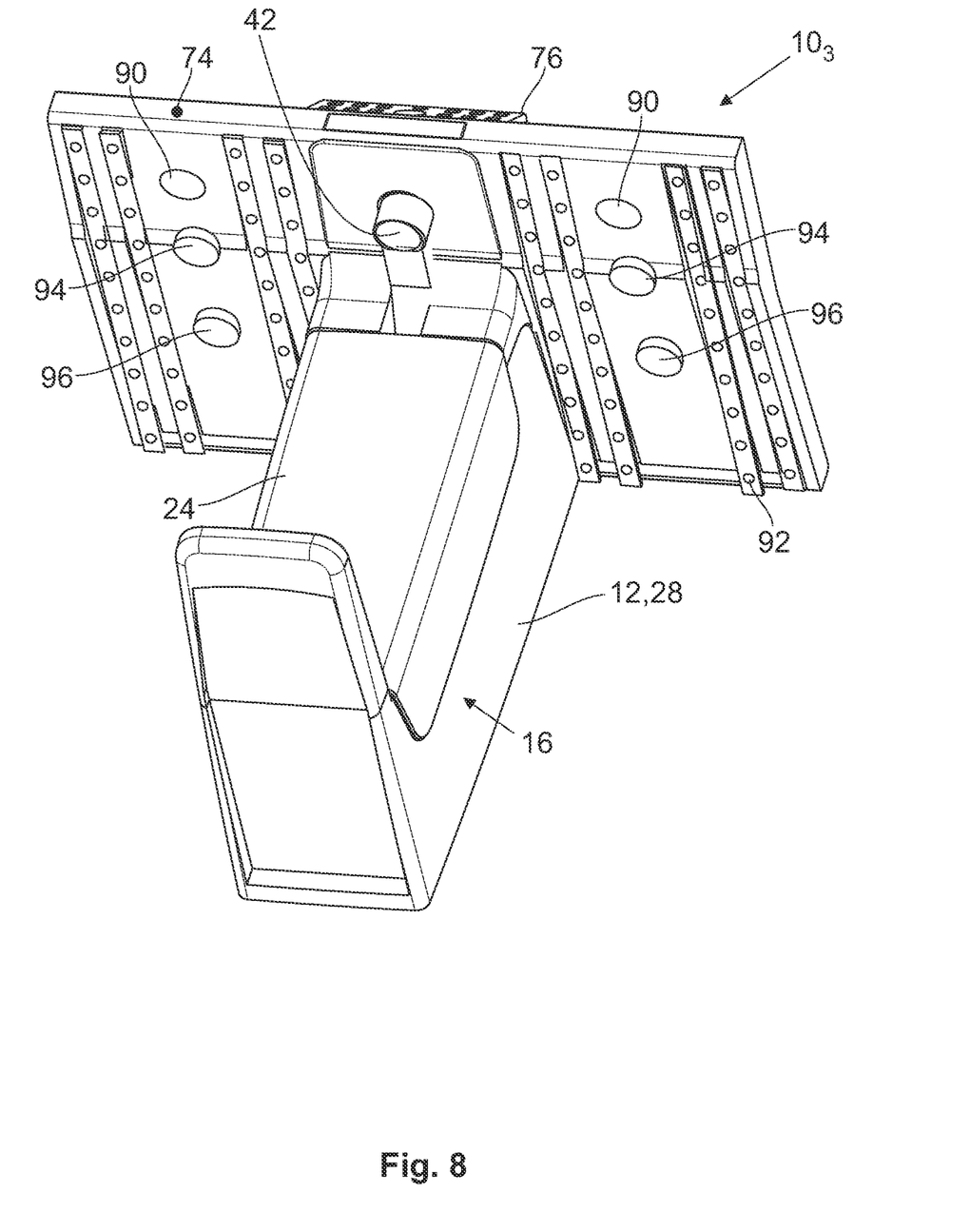
FIG. 8 shows a second perspective representation of the third embodiment of the device according to the proposal.

FIGS. 7 and 8 show a third embodiment of the device $10_3$ according to the proposal on the basis of perspective representations. The device $10_3$ according to the third embodiment comprises all the features of the second embodiment of the device $10_2$ and is consequently based thereon. In particular, according to the third embodiment, the device $10_3$ has the drive unit 48, which is not visible in FIGS. 7 and 8. Only the additional features are referred to below.

The device $10_3$ according to the third exemplary embodiment has a top panel 74, which is connected to the housing 12, for example by means of a latching connection. However, the top panel 74 can also be manufactured as an integral part of the housing 12. In FIG. 7, one looks at the top of the top panel 74. The top panel 74 protrudes to the left and to the right beyond the housing 12. Attached to the top panel 74 is a display 76, with which user-related data and device-related data or other data can be displayed. To this end, the display 76 has a display section 78.

Furthermore, a user identification device 80 is arranged in the display 76, which comprises a readout unit 82 for reading out an RFID transponder 84, which is only shown here in principle. Alternatively or cumulatively, the user identification device 80 comprises a second camera 86, which is also arranged in the display 76.

The display 76 also comprises a number of keypads 88, in this case twelve keypads 88, each of the keypads 88 being assigned to a specific activity related to a disinfection process. This will be discussed in more detail later.

FIG. 8 shows the device $10_3$ according to the third embodiment on the basis of a second perspective representation, in which one can look at the underside of the top panel 74. Two ultrasonic sensors 90 are arranged on the underside of the top panel 74 and can emit ultrasound and detect reflected ultrasound.

Furthermore, a plurality of light sources 92, which can emit ultraviolet radiation, are arranged in the form of a strip on the underside of the top panel 74. In the illustrated embodiment, these light sources 92 are designed as LED strips which extend from the front edge to the rear edge of the top panel 74.

In addition, two UV sensors 94 are provided, which are also attached to the underside of the top panel 74 and can detect reflected UV rays.

Furthermore, two first cameras 96 are arranged on the underside of the top panel 74. The ultrasonic sensors 90 as well as the light sources 92, the UV sensors 94 and the two first cameras 96 interact with the monitoring unit 54, which is not visible here.

The device $10_3$ according to the third exemplary embodiment can be operated in the following manner.

A user, for example an employee of a hospital who wants to disinfect his hands, holds an RFID transponder 84 assigned to him in front of the readout unit 82. Depending on the design of the device $10_3$, the second camera 86 can instead detect, for example, the facial features of the employee. The readout unit 82 and the second camera 86 may also be operated in parallel with one another to provide redundancy. The goal is to identify the employee. If the employee is successfully identified, a corresponding piece of information can be output on the display section 78 of the display 76. In the event of an unsuccessful identification, a corresponding error message can be issued.

In the event of a successful identification, the employee can now select one of the keypads 88, which is assigned to the activity which the employee is currently planning to perform, for example a catheter change. The employee then holds his hands under the first camera 96 and/or under the ultrasonic sensor 90. The device $10_3$ now checks whether the employee is wearing jewelry such as a ring or has artificial nails. If this is the case, a corresponding notification is issued, according to which the applicable regulations have been violated. If the employee has no artificial nails and is not wearing jewelry, a corresponding OK message is issued and the employee can now move his hands under the delivery opening 42. This movement is registered by the motion sensor 50, not shown in FIG. 8 (see for example FIGS. 4 and 5), as a result of which the drive unit 48 is activated and a certain amount of the fluid is delivered. The amount of the fluid delivered can depend on the selected activity. A fluorescent additive is added to the fluid, which becomes visible in interaction with the UV rays emitted by the light sources 92. After the employee has massaged the fluid into his hand surfaces, he can already see for himself whether the entire hand surface has been wetted by the fluid or whether areas have been missed. To this end, the user holds his hands under the light sources 92, which have been switched on at the same time as or shortly after the activation of the drive unit 48. By means of the UV sensors 94 and/or by means of the first cameras 96, it can be checked by means of the device $10_3$ whether the entire hand surface has been wetted by the fluid or whether areas have been missed. If the entire hand surface is wetted by the fluid, a further OK message is issued, indicating that the hand disinfection is successfully completed. If areas have been missed, the fluid must be massaged again or additional fluid must be requested.

All the data which have been logged by the monitoring unit 54 of the device 10₃ during the hand disinfection are transmitted by means of the transmitting and receiving unit 60 (cf. FIGS. 4 and 5) to the external units 62. The external units 62 document that the employee concerned has carried out the relevant activity after he has disinfected his hands according to the regulations. The information that the hand disinfection has been successfully completed can also be used to grant the relevant employee access to the patient. To this end, the external units 62 can interact with a door opener which opens the door to the room in which the patient is located only after the hand disinfection has been successfully completed.

It may be prescribed that the hands must be disinfected again when the employee has completed the activity in question. Then the procedure described above can be performed again. This hand disinfection is also documented.

Depending on the selected activity and the configuration of the device 10₃, the above-mentioned steps for hand disinfection can also be carried out in a different sequence. In addition, additional steps may be provided or steps may be omitted.

LIST OF REFERENCE NUMBERS

10 Device
10₁-10₃ Device
12 Housing
14 Cavity
16 Opening
18 Container
20 Pump and metering unit
22 Actuating lever
24 Closure body
26 Receiving opening
28 Outer housing surface
30 Pump and metering unit outer surface
32 Closure body outer surface
33 Antibacterial surface
34 Superhydrophobic surface
36 Pump plunger
38 First spring
40 Channel
42 Delivery opening
44 Suction tube
45 Hose
46 Non-return valve
47 Second spring
48 Drive unit
49 Fastening device
50 Motion sensor
51 Adapter unit
52 Ultrasonic sensor, proximity sensor
53₁, 53₂ Tubular section
54 Monitoring unit
55 Sealing body
56 Level sensor
57 Opening
58 Temperature sensor
59 Contact surface
60 Transmitting and receiving unit
60₁-60₃ First to third receiving unit
62 External unit
62₁-62₃ First to third external unit
64 System
66 Own pump and metering unit
68 Delivery opening
70 Support body
71 Circuit board
72 Further cavity
73 Battery
74 Top panel
75 Ethernet connection
76 Display
78 Display section
80 User identification device
82 Readout unit
84 RFID transponder
86 Second camera
88 Keypad
90 Ultrasonic sensor
92 Light sources
94 UV sensors
96 First camera

The invention claimed is:

1. A system for monitoring a device (10) for delivering fluid, comprising:
    the device (10) for delivering fluid, comprising:
        a housing (12) which encloses a cavity (14) into which a container (18) for holding the fluid can be installed, the housing (12) further having an outer housing surface (28);
        a pump and metering unit (20) which can be connected or is connected to the housing (12), and which can be connected to the container (18) in a detachable manner, whereby the pump and metering unit (20) pumps the fluid out of the container (18) for delivery thereof;
        a monitoring unit (54) with which device-related and/or user-related data can be collected and stored;
        a display (76) interacting with the monitoring unit (54) for entering and displaying the user-related data and/or the device-related data; and
        a transmitting and receiving unit (60) for data exchange with external units (62);
    a first external unit (62₁) on which user-related data are stored, which can be read out by means of the transmitting and receiving unit (60); and
    a second external unit (62₂), on which the user-related data and device-related data can be deposited and evaluated, the second external unit (62₂) having a second transmitting and receiving unit (60₂) for data exchange with the transmitting and receiving unit (60) of the device (10).

2. The system according to claim 1, characterized in that at least one ultrasonic sensor (90) is arranged on the outer housing surface (28).

3. The system according to claim 1, characterized in that a number of light sources (92) which emit ultraviolet radiation are arranged on the outer housing surface (28).

4. The system according to claim 3, characterized in that the device comprises at least one UV sensor (94) for registering the ultraviolet rays reflected by the hands of a user.

5. The system according to claim 3, characterized in that at least one first camera (96) is arranged on the outer housing surface (28).

6. The system according to claim 1, characterized in that the device (10) has a user identification device (80) with which the identity of the user of the device (10) can be established.

7. The system according to claim 6,
characterized in that the user identification device (80) has a readout unit (82) for reading out an RFID transponder (84).

8. The system according to claim 7,
characterized in that the user identification device (80) further comprises a second camera (86).

9. The system according to claim 8,
characterized in that the readout unit (82) and/or the second camera (86) are arranged in the display (76).

10. The system according to claim 1,
characterized in that a number of keypads (88) is arranged in the display (76), each of the keypads (88) being assigned to a specific activity related to a disinfection process.

11. The system according to claim 1, further comprising:
a level sensor (56) for determining the level of the fluid in the cavity (14); and/or
a temperature sensor (58) for determining the temperature of the fluid in the cavity (14).

12. The system according to claim 1, further comprising:
a drive unit (48) that can be activated by means of a motion sensor (50) that can be triggered in a contactless manner, and the motion sensor (50) comprises an ultrasonic sensor or a proximity sensor.

13. The system according to claim 1,
characterized in that the outer housing surface (28) comprises an antibacterial surface (33) and/or as a superhydrophobic surface (34).

14. The system according to claim 1,
characterized in that the second transmitting and receiving unit (602) is set up in such a way that a data exchange with a third external unit (623) is made possible.

* * * * *